US00PP27278P2

(12) United States Plant Patent
Remphrey

(10) Patent No.: US PP27,278 P2
(45) Date of Patent: Oct. 18, 2016

(54) ***ACER GINNALA* TREE NAMED 'JEFUM'**

(50) Latin Name: *Acer ginnala*
Varietal Denomination: JefUM

(71) Applicant: University of Manitoba, Winnipeg (CA)

(72) Inventor: William R. Remphrey, Winnipeg (CA)

(73) Assignee: UNIVERSITY OF MANITOBA, Winnepeg (CA)

( * ) Notice: Subject to any disclaimer, the term of this patent is extended or adjusted under 35 U.S.C. 154(b) by 47 days.

(21) Appl. No.: 14/121,758

(22) Filed: Oct. 14, 2014

(51) Int. Cl.
*A01H 5/12* (2006.01)

(52) U.S. Cl.
USPC ..... Plt./224

(58) Field of Classification Search
USPC ..... Plt./224
See application file for complete search history.

*Primary Examiner* — Anne Grunberg
(74) *Attorney, Agent, or Firm* — Penny J. Aguirre

(57) ABSTRACT

A new cultivar of *Acer ginnala*, 'JefUM', that is characterized by its clump forming plant habit with 3 to 4 stem clumps consistently maintained, its fall foliage that is red-purple in color, its clean and disease-free three-lobed foliage, and its resistance to iron chlorosis when grown in alkaline soils.

2 Drawing Sheets

Botanical classification: *Acer ginnala.*
Variety denomination: 'JefUM'.

BACKGROUND OF THE INVENTION

The present invention relates to a new and distinct cultivar of *Acer ginnala*, and will be referred to hereafter by its cultivar name, 'JefUM'. 'JefUM' is a deciduous tree grown for use as a landscape plant.

The Inventors selected the new cultivar, 'JefUM', as a seedling in Winnipeg, Manitoba, Canada in the summer of 2000. The seedbed had been planted with seeds collected from an unnamed and unpatented open pollinated plant of *Acer ginnala.*

Asexual reproduction of the new cultivar was first accomplished by softwood stem cuttings by the Inventor in Winnipeg, Canada in the summer of 2002. Asexual propagation of 'JefUM' by softwood stem cuttings has shown that the unique features of the new cultivar are stable and are reproduced true to type in successive generations.

SUMMARY OF THE INVENTION

The following traits have been repeatedly observed and represent the characteristics of the new cultivar. These attributes in combination distinguish 'JefUM' as a new and unique cultivar of *Acer.*

1. 'JefUM' exhibits a clump forming plant habit with 3 to 4 stem clumps consistently maintained.
2. 'JefUM' exhibits fall foliage that is red-purple in color.
3. 'JefUM' exhibits clean, disease-free three-lobed foliage.
4. 'JefUM' exhibits good resistance to iron chlorosis when grown in alkaline soils.

The parent of 'JefUM' differs from 'JefUM' in being less resistant to iron chlorosis. 'JefUM' can also be compared to the *Acer* cultivars 'Ruby Slippers' (not patented) and 'Flame' (not patented). 'Ruby Slippers' is similar to 'JefUM' in being the same overall height and width. 'Ruby Slippers' differs from 'JefUM' in having bright red samaras, in having fall foliage that is bright red in color, in being cold hardy to U.S.D.A. Zone 3, and in having a single stem plant habit. 'Flame' is similar to 'JefUM' in having a clump forming habit and in being hardy to U.S.D.A. Zone 2. 'Flame' differs from 'Jefrum' in having fall foliage that is orange-red in color.

BRIEF DESCRIPTION OF THE DRAWINGS

The accompanying colored photographs illustrate the overall appearance and distinct characteristics of the new *Acer*, 'Jefrum'. The photographs were taken of a 7 year-old plant of 'JefUM' as grown outdoors in the ground in Portage la Prairie, Canada.

Figure 1:
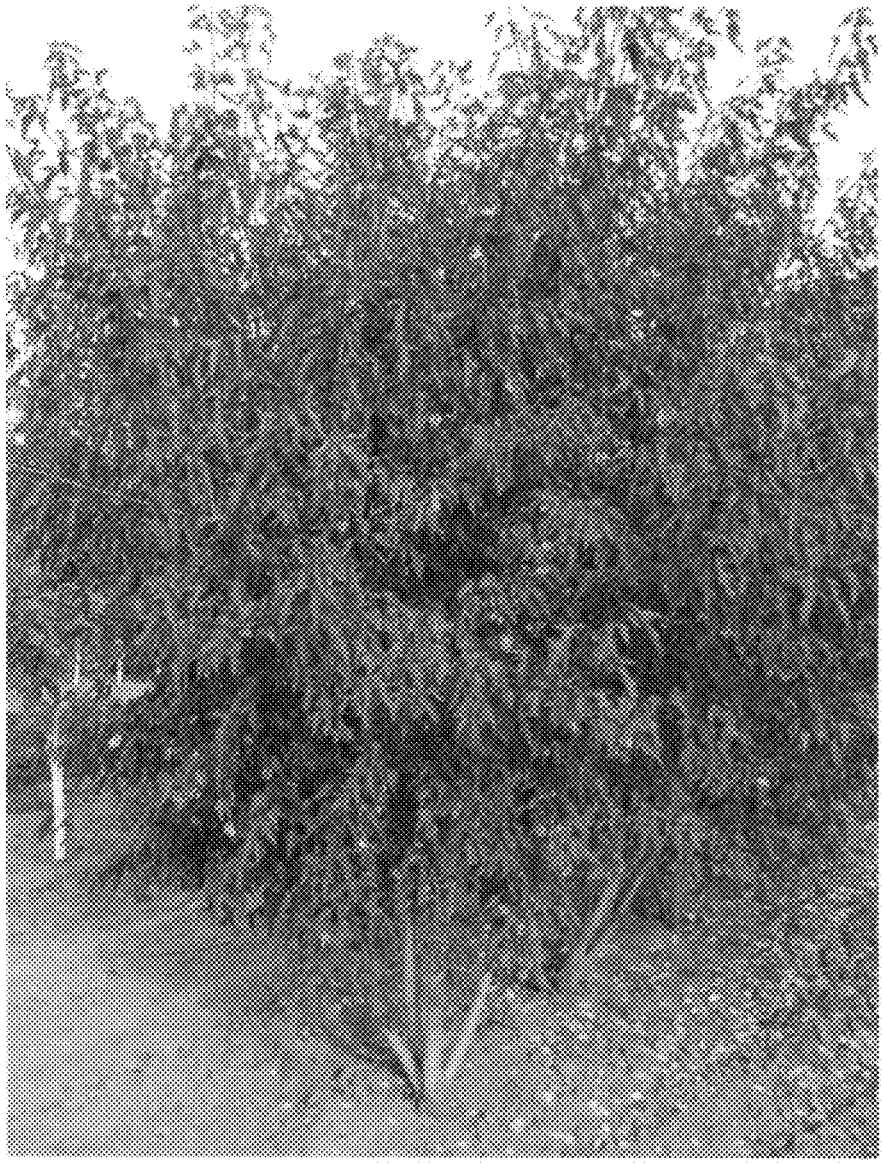
FIG. 1 provides an overall view of the foliage and plant habit of 'JefUM' in fall.
Figure 2:
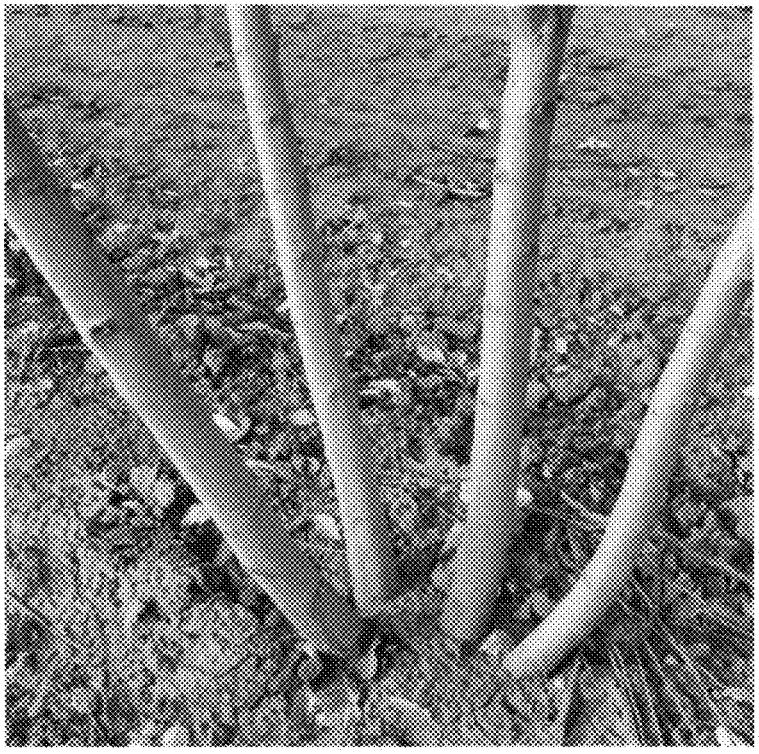

The photograph in FIG. 2 provides a view of the multi-stem habit of 'JefUM'.

Figure 3:
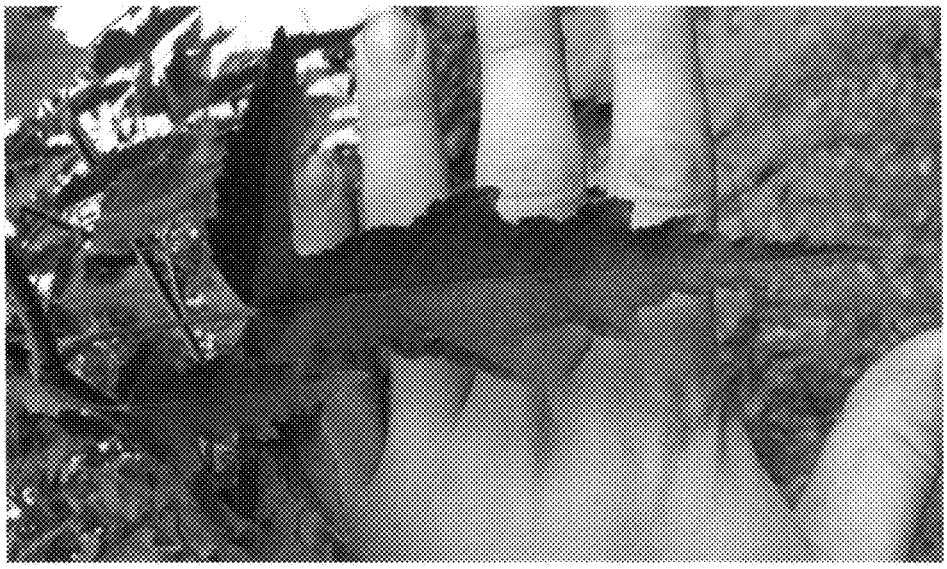

The photograph in FIG. 3 provides a close-up view of the upper surface of leaves of 'JefUM' in fall.

The colors in the photographs are as close as possible with the photographic and printing technology utilized and the color values cited in the Detailed Botanical Description accurately describe the colors of the new *Acer.*

DETAILED BOTANICAL DESCRIPTION

The following is a detailed description of a three-year old plant of the new cultivar as observed outdoors in a 2-gallon container in St. Paul, Minn. for one year. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Plant type.*—Deciduous tree; grown as a multi-stemmed large shrub.

*Plant habit.*—Clump forming tree (consistently maintains 3 to 4 stem clumps).

*Height and spread.*—An average of 6 m in height and spread when mature in the landscape.

*Cold hardiness.*—At least to U.S.D.A. Zone 2.

*Diseases and pests.*—Good resistance to iron chlorosis has been observed.

*Root description.*—Fibrous, freely branched.

*Propagation*—Stem cuttings.

*Growth rate.*—Vigorous.

Branch description:

*Shape.*—Round.

*Stem color.*—Mature wood 199A with striations of 199D, new growth; 166A.

*Stem size.*—Main stems; average of 60 cm in length and 7 mm in width, secondary branches; average of 30 cm in length and 4 mm in width.

*Stem surface.*—New growth glabrous, mature wood finely barked.

*Internode length.*—Highly variable.

*Branching.*—Multi-branched, 3 to 4 main stems and 4 secondary branches per main branch.

Foliage description:

*Leaf shape.*—Broadly ovate to lanceolate in overall outline.

*Leaf division.*—Simple.

*Leaf base.*—Hastate.

*Leaf apex.*—Acuminate.

*Leaf fragrance.*—None.

*Leaf venation.*—Pinnate, 163C on upper surface and 160C on lower surface on mature summer foliage.

*Leaf margins.*—Primarily tri-lobed, lobe margins serrated to slightly lobed.

*Leaf arrangement.*—Opposite.

*Leaf aspect.*—Held upright on petioles held at about a 45° angle from branch.

*Leaf attachment.*—Petiolate.

*Leaf internode length.*—An average of 3 cm with new growth at apex an average of 1 cm.

*Leaf surface.*—Glabrous on upper and lower surface.

*Leaf size.*—Up to 9 cm in length and 7 cm width, lobes; center lobe up to 7.5 cm in length and 4 cm in width, side basal lobes up to 4 cm in length and 1.8 cm in width.

*Leaf color.*—Newly expanded leaves in summer; upper surface 137C and lower surface 137D, mature foliage; upper surface 137A, lower surface 138A, fall foliage; Upper and lower surface; becoming increasingly suffused with N77A with cool temperatures with some tips on newer growth 60B to 60C, leaves with full sun exposure at N77A.

*Petioles.*—Up of 4.5 cm in length and 1.5 mm in width, held horizontal and slightly drooping to about a 45° angle upward from branch, color 183B on upper surface and 160C on lower surface.

*Stipules.*—None.

Inflorescence description: (Non-showy).

*Blooming period.*—Late May to early June in Minnesota.

*Inflorescence.*—Terminal and upper axillary complex corymbs of small flowers, about 4 cm in width and 4 cm in length.

*Inflorescence number.*—An average of 3 per secondary branch.

*Lastingness of inflorescence.*—An average of 10 days.

*Flowers.*—Campanulate in shape, about 5 mm in length and 3 mm in width, about 50 per corymb, slightly fragrant, 5-merous.

*Flower buds.*—3 mm in length and 2 mm in width, 145C in color, ovate in shape, glabrous surface texture.

*Petals.*—5, an average of 1 mm in length and 0.5 mm in width, 11C in color, elliptic in shape, glabrous surface texture, entire margin, acute apex, cuneate base, curled inward around reproductive organs.

*Sepals.*—5, an average of 2 mm in length and 1 mm in width, 11C in color, elliptic in shape, glabrous surface texture, entire margin, acute apex, cuneate base, curled inward around petals and reproductive organs.

*Peduncle.*—Moderate strength, main peduncle an average of 3.5 cm in length and 1.5 mm in length, secondary peduncles an average of 1.2 cm in length and 1 mm in width, 145B to 145C in color, glabrous surface texture.

*Pedicels.*—Moderate strength, average of 2 mm in length and 0.5 mm in width, 145C in color, glabrous surface texture.

Reproductive organs:

*Pistil.*—1, bifid stigma, 145B to 145C in color, style 150D in color and 2.5 mm in length, ovary is superior, 2 winged, 2 mm in width and 1.5 mm in length, 144B in color and highly pubescent.

*Stamens.*—Up to 8, linear in shape, 157D in color, anthers and pollen not distinguishable.

Fruit and seed: Samaras, 2-winged, an average of 1.2 cm in length and 4 mm in width, 144A in color and suffused on wings with 60A and drying to 161A in color, single seed an average of 3 mm in diameter and N199B in color.

It is claimed:

1. A new and distinct cultivar of *Acer ginnala* tree named 'JefUM' as herein illustrated and described.

* * * * *